United States Patent [19]

Malyshev et al.

[11] 4,144,888
[45] Mar. 20, 1979

[54] DEVICE FOR TREATMENT BY LASER EMISSION

[76] Inventors: Boris N. Malyshev, ulitsa Butlerova, 24, kv. 219; Vladimir N. Prozorov, Varshavskoe shosse, 87, kv. 89; Igor I. Gonel-Budantsev, 1 Dobryninsky pereulok, 9, kv. 5, all of Moscow, U.S.S.R.

[21] Appl. No.: 723,546

[22] Filed: Sep. 15, 1976

[51] Int. Cl.² .............................................. A61N 5/01
[52] U.S. Cl. .............................. 128/303.1; 219/121 L; 350/96.10
[58] Field of Search ......... 128/303 R, 303.1, 395-396; 331/DIG. 1; 350/299, 301, 96 WG, 96 T; 219/121 L, 121 LM

[56] References Cited

U.S. PATENT DOCUMENTS

| | | | |
|---|---|---|---|
| 3,481,340 | 12/1969 | McKnight et al. | 128/395 |
| 3,528,424 | 9/1970 | Ayres | 128/303.1 |
| 3,653,384 | 4/1972 | Swope | 219/121 L |
| 3,828,788 | 8/1974 | Krasnov et al. | 128/303.1 |
| 3,848,104 | 11/1974 | Locke | 219/121 L |
| 3,913,582 | 10/1975 | Sharon | 128/303.1 |
| 3,920,951 | 11/1975 | Chovan et al. | 219/121 L |
| 3,986,767 | 10/1976 | Rexer et al. | 350/299 |

*Primary Examiner*—William E. Kamm
*Attorney, Agent, or Firm*—Lackenbach, Lilling & Siegel

[57] ABSTRACT

A wavebeam guide transmitting the laser emission to a selected region of a patient comprises only two mirrors; an input mirror and a output mirror, which mirrors are mounted in units of the device connected by a telescopic shaft. The input mirror is mounted so that it can rotate about an axis coinciding with the axis of the laser beam falling thereupon and about an axis perpendicular thereto. The output mirror can also rotate about the axis of the laser beam falling thereon and about the perpendicular axis. Both mirrors can also rotate together in relation to the axes of rotation of the input mirror and the distance between the mirrors can be changed by means of the telescopic shaft. An aiming grip is provided to carry a focusing lens mounted so that it can rotate about the axis of the laser beam reflected by the output mirror.

2 Claims, 3 Drawing Figures

DEVICE FOR TREATMENT BY LASER EMISSION

BACKGROUND OF THE INVENTION

The invention relates to medical equipment and, in particular, to a device for treatment by laser emission.

Known in the art are devices for treatment by laser emission, for example, a device for laser surgical treatment described in French Pat. No. 2,203,090, comprising a foundation, a horizontally positioned laser, a seven-mirror three-joint wavebeam guide featuring an aiming grip on its end, a balancing device with a counterweight. The balancing device with the counterweight serves to balance the wavebeam guide.

The known device is deficient since its wavebeam guide possesses great inertia due to the large number of mirrors, mirror mounting units, constructional fixing and connecting elements of the mirror mounting units, as well as the balancing device and the heavy counterweight. In order to move the end aiming grip in three dimensions the surgeon has to apply substantial physical efforts to overcome the inertia of the system.

It is an object of this invention to reduce the inertia of the wavebeam guide.

Another object of this invention is to provide more favourable conditions for a surgeon.

Yet object of this invention is to increase the reliability of the device for treatment by laser emission.

BRIEF SUMMARY OF INVENTION

These and other objects of the invention are achieved by the disclosed device since the wavebeam guide comprises only two mirrors, an input mirror and an output mirror, said mirrors being mounted so that they can rotate about two axes each, one axis coinciding with the axis of the laser beam falling thereupon and the other axis perpendicular to this first axis, the distance between said mirrors can be changed along the longitudinal axis of the laser beam reflected by the input mirror and the two mirrors can rotate together about the axes of rotation of the input mirror, besides the aiming grip of the wavebeam guide is mounted so that it can rotate about the axis of the laser beam reflected by the output mirror and rotate together with the output mirror about the axis perpendicular to the axis of the laser beam falling on the output mirror.

In one embodiment of the disclosed device the laser is inclined in the vertical plane or placed vertically. The input and output mirrors of the wavebeam guide are installed in mirror mounting units at the ends of the telescopic shaft which axis coincides with the axis of the laser beam reflected by the input mirror. When the laser is inclined in the vertical plane, its position permits larger angular turning range of the telescopic shaft rotating about the first of said axes as compared to the vertical position of the laser. An aiming grip is secured on the output mirror mounting unit so that it can rotate about the axis of the laser beam reflected by the output mirror. The telescopic shaft is secured as a flexible cantilever on the output mirror mounting unit comprising springs balancing the telescopic shaft as a whole and its linearly moving part in particular with respect to the rotation axis perpendicular to the laser beam falling on the input mirror and along the axis of the laser beam reflected by the input mirror, respectively. The units for mounting the input and output mirrors are mirror joints for turning the beam, comprising a mirror provided with a rotating drive with a gear ratio of 1:2, two housing members hinged to each other, a mirror rotating drive includes a strip permanently under tension and directed by a roller and rigidly fixed on two drums located coaxially with the joint. The smaller drum is secured on the emission output housing members and the larger drum has only one layer of the strip.

BRIEF DESCRIPTION OF DRAWINGS

The invention will now be described in greater detail with reference to a specific embodiment thereof, taken in conjunction with the accompanying drawings, wherein.

DETAILED DESCRIPTION OF THE INVENTION

Figure 1:
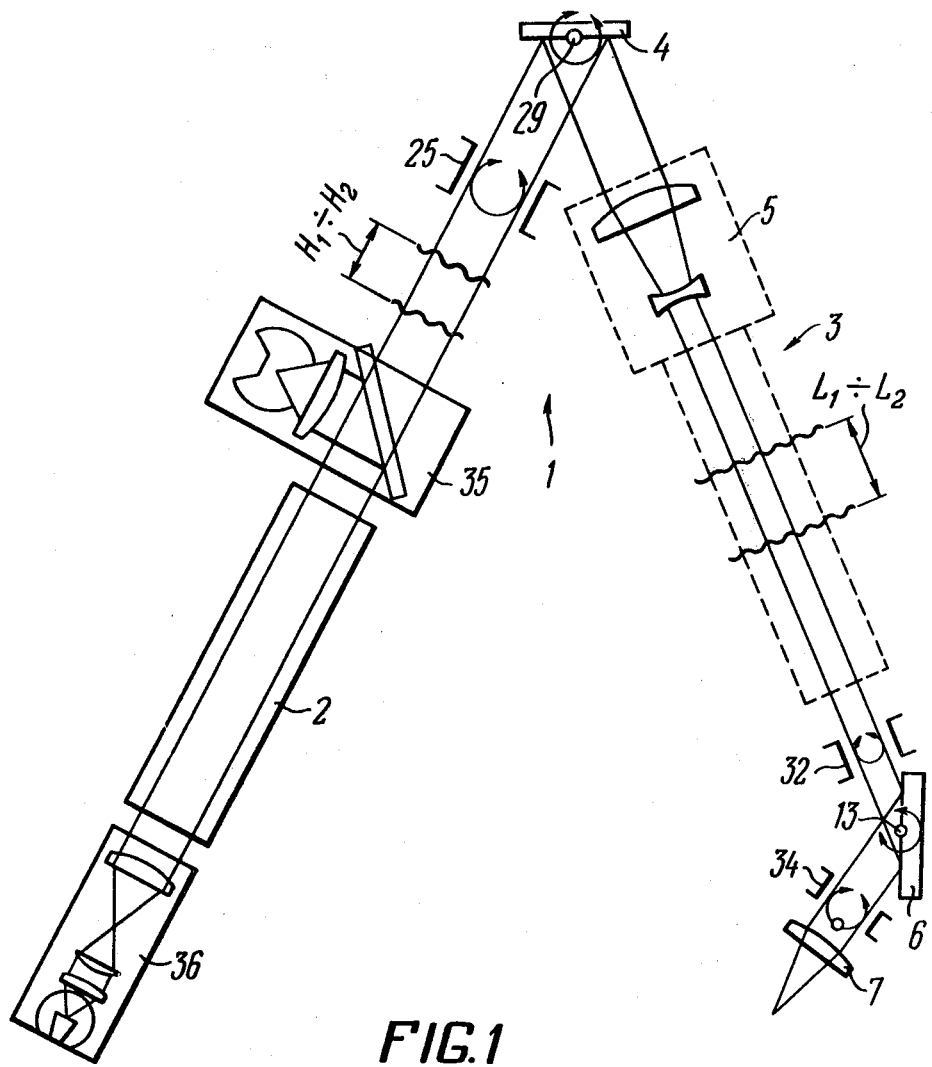
FIG. 1 shows an optical diagram of the disclosed device, according to the invention.

A device 1 (FIGS. 1 and 2) comprises a laser 2, a wavebeam guide 3, an input mirror 4 of the wavebeam guide, an optical telescopic system 5, and output mirror 6 of the wavebeam guide, a focusing lens 7.

The laser can be of any known type, providing it ensures the required emission power.

Continuous wave argon and carbon dioxide lasers, pulsing ruby and neodymium garnet lasers, as well as continuous wave neodymium garnet lasers can and have been used. The input mirror 4 and the output mirror 6 of the wavebeam guide 3 can be made, depending on the type of laser employed, as plates of an optical glass covered by multi-layer reflecting dielectric coats, of stainless steel with or without gold coating. The optical elements of the optical telescopic system 5 and the focusing lens 7 are made of a material optically transparent in the wavelength of the laser emission and provided with dielectric coats.

Figure 2:
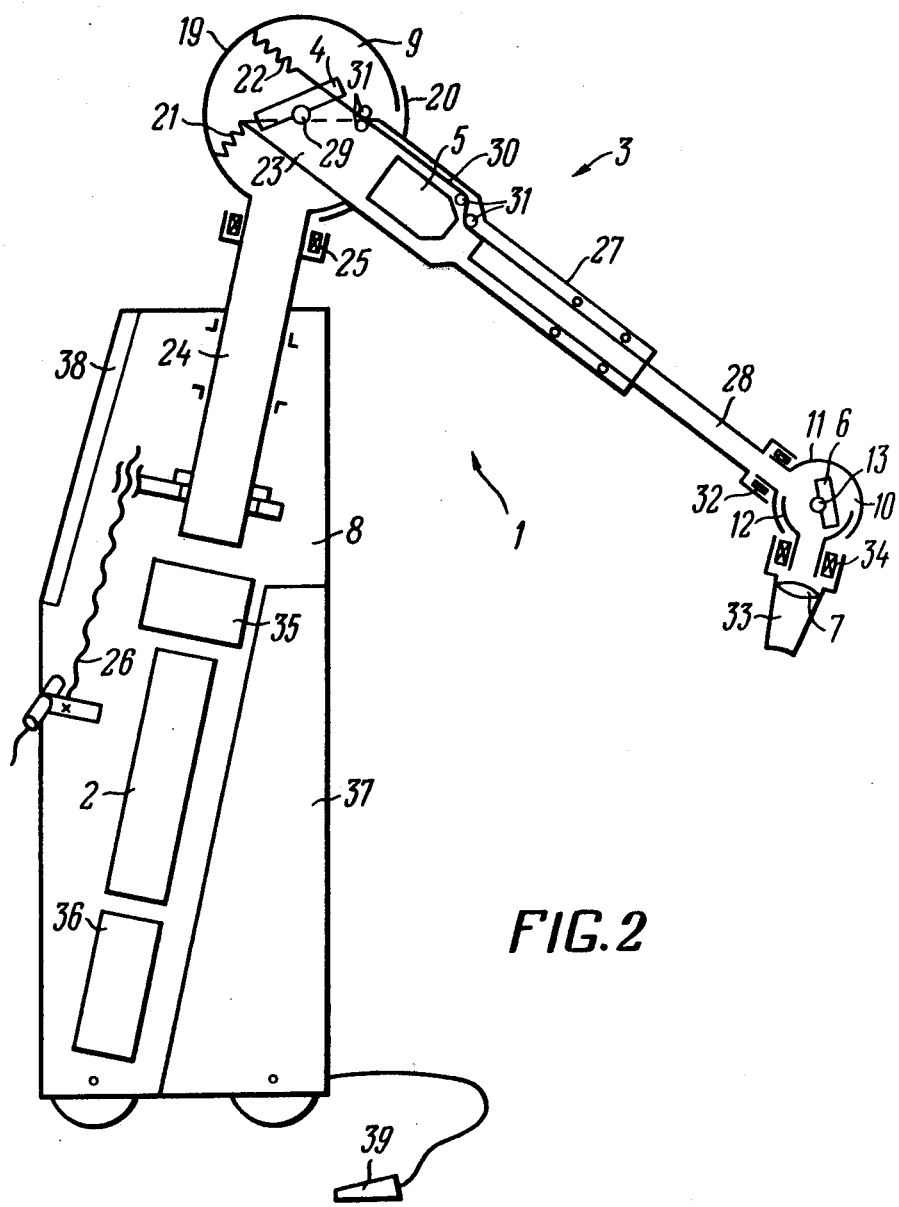
FIG. 2 shows a mechanical diagram of the disclosed device, according to the invention.

Referring to FIG. 2, the laser 2 is rigidly secured in an inclined vertical position in a stand 8. The inclination angle should not exceed 45° with respect to the vertical.

The input mirror 4 and the output mirror 6 of the wavebeam guide 3 are hinged in respective mirror mounting units 9 and 10 (FIG. 2).

Figure 3:
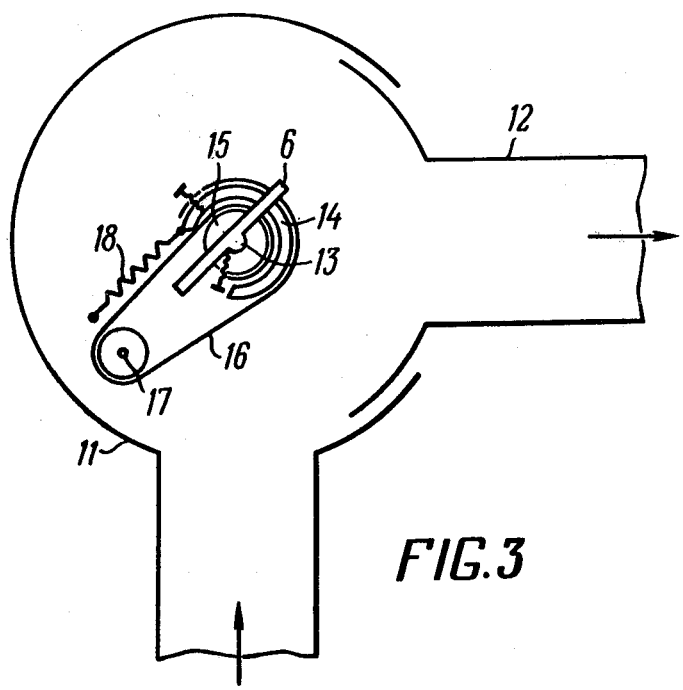
FIG. 3 shows a diagram of an output mirror mounting unit, according to the invention.

The mirror mounting unit 10 (FIG. 3) comprises an input housing member 11 of the unit housing and an output housing member 12 of the unit housing hinged so that they can turn with respect to each other around an axis 13 passing normally to the drawing plane through the intersection point of their longitudinal symmetry axis. The unit housing members 11 and 12 are metal half-cylinders featuring tubes entering into each other so that they can be mutually turned. It is evident that any shape of the housing can be used instead of the cylindrical shape, e.g. spherical. The mirror 6 turns about the same axis 13. The mirror 6 (FIG. 3) is secured on a drum 14 and a drum 15 is mounted coaxially therewith and rigidly connected to the housing member 12.

The drum 14 is connected to the drum 15 by a flexible strip 16 secured on each of the drums. The strip 16 is passed over a guiding roller 17 attached on the member 11. A spring 18 keeps the strip 16 stretched.

The diameter of the drum 14 is twice the diameter of the drum 15. The strip 16 is 0.05–0.08 mm thick. The gear ratio of such a mechanism is equal to ½.

The emission directed along the axis of symmetry of the member 11 is reflected by the mirror 6 along the axis of symmetry of the member 12 as indicated by arrows. When the member 12 is turned about the axis 13 to a certain angle, the drum 15 is turned too and it pulls or releases the strip 16 attached thereto. The strip 16 rotates the drum 14 together with the mirror 6 to the angle which is half the rotation angle of the drum 15. The incidence angle being equal to the reflection angle, the beams always come out along the axis of the housing member 12 with a maximum deflection less than one angular minute.

The construction of the unit 9 carrying the mirror 4 and comprising an input housing member 19 and an output housing member 20 is similar to the construction of the mounting unit of the mirror 6 but has additional springs 21, 22 and a bracket 23. The input housing member 19 of the unit is secured on a tube 24 so that it can rotate about the vertical axis on bearings 25. The tube 24 is mounted in the stand 8 so that it can be lifted and lowered by a lifting mechanism 26.

The mirror mounting units 9 and 10 are connected by a hollow telescopic shaft comprising a linearly unmovable part 27 and a linearly movable part 28. A telescopic optical system 5 is installed in the linearly unmovable part 27 of the telescopic shaft. The part 27 of the telescopic shaft is rigidly fitted as a cantilever on the output housing member 20 of the mounting unit 9, which can rotate about a rotation axis 29 of the mirror 4, perpendicular to the drawing plane. The linearly movable part 28 of the telescopic shaft is balanced by the spring 22, which one end is secured on the housing member 19 of the mounting unit 9 and the other end is secured to the part 28 through a cable 30 directed by rollers 31.

The telescopic shaft is on the whole balanced by the spring 21 with respect to the rotation axis 29. The spring 21 is secured by one end on the housing member 19 and by the other end on the bracket 23 of the output housing member 20 of the mounting unit 9 carrying the mirror 4.

The input housing member 11 of the mounting unit 10 of the mirror 6 is connected via a bearing 32 to the linearly movable part 28 of the telescopic shaft so that it can rotate about the axis of symmetry of the telescopic shaft.

The focusing lens 7 secured in is an aiming grip 33 which is connected through a bearing 34 to the output housing member 12 of the mirror mounting unit 10 so that it can be rotated about its own. The aiming grip 33 can rotate about the axis 13 together with the housing member 12.

For convenience the disclosed device is provided with an emission dose meter 35 and a source 36 of parallel lighting located in the stand 8. Besides, the stand 8 houses a power supply unit 37 and a control board 38 of the laser 2. The device is provided with a foot pedal 39 for switching on the laser 2.

The disclosed device operates as follows.

The lighting source 36 is switched on by the control board 38 and the laser 2 operating continuously or in pulses is switched on by the foot pedal 39. The laser emission beams pass through the emission dose meter 35 which registers laser emission and fall on the input mirror 4 of the wavebeam guide. The mirror 4 reflects and directs the laser emission beam and the beam of the light source into the telescopic system 5 which reduces their cross sections.

After the telescopic system 5 the laser beam and the light beam pass through the inner space of the telescopic shaft and fall onto the output mirror 6 which directs the beams through the focusing lens 7 to the object.

The beams remain centered along the axes of symmetry of the wavebeam guide during rotation of the guide 3 about the inclined vertical axis on the bearings 25, turning of the telescopic shaft 27-28 about the axis 29 and reciprocating of the part 28 of the telescopic shaft, when the mounting unit 10 of the mirror 6 rotates on the bearings 32 and the aiming grip 33 rotates on the bearings 34 about the axis 13.

As a result the physician sets the height of the wavebeam guide 3 by the mechanism 26 and can bring the focused or unfocused emission beam to the object by means of an aiming grip 33 along any space curve. The spot of the laser beam is visible due to the visible light source 36.

In the disclosed device the physician uses but a minimum effort to move the spot since the aiming grip can move in three dimensions and the wavebeam guide has low inertia. Low inertia results since the wavebeam guide has only two mirrors and is provided with balancing springs. The balancing springs have a substantially smaller mass as compared to other parts of the wavebeam guide and practically do not contribute to the its inertia.

What is claimed is:

1. A device for treatment by laser emission, comprising: a laser; a wavebeam guide for transmission of emission of said laser to a selected point of a patient, said wavebeam guide being provided with only two mirrors: an input mirror which is first in the direction of the laser emission propagation and the other being an output mirror located beyond the first mirror in the direction of the laser emission propagation; mounting units for mounting said mirrors so that they can rotate about two axes, one axis coinciding with the axis of the laser beam incident thereon and the other axis perpendicular to said one axis, the mirrors having means for rotation together in relation to the rotation axes of said input mirror, said mounting units also being mounted for variably adjusting the distance therebetween in order to change the distance between said mirrors along the axis of the laser beam reflected by the input mirror; an aiming grip mounted on said wavebeam guide for rotation about the axis of the laser beam reflected by said output mirror and for rotation together with said output mirror about the axis perpendicular to the axis of the laser beam incident on said output mirror; a focusing lens mounted in said grip, said mirror mounting units securing said input and output mirrors at the ends of said wavebeam guide the axis of which coincides with the axis of the laser beam reflected by said input mirror, each of said mirror mounting units comprising two housing members including means for moving the same relative to each other about a common rotation axis; a mirror rotating drive disposed inside each of said housing members, each drive comprising two coaxial drums having a ratio of diameters equal to one to two and working surfaces, said drums being mounted coaxially about a rotation axis of the respective housing members, and a ribbon engaging said working surfaces of said drums, said ribbon being permanently in a state of tension; a guiding roller for guiding said ribbon mounted at a rotation axis spaced from the rotation axis of the respective housings and drums to thereby provide a gear ratio equal to one to two between said drums; and means for rigidly securing the smaller one of the drums to one of said housing members; and the larger drum being rigidly secured to the respective mirror rotatable about said rotation axis of said housings.

2. A device for treatment by laser emission, comprising: a laser; a wavebeam guide for transmission of emission of said laser to a selected point of a patient, said wavebeam guide being provided with only two mirrors: an input mirror which is first in the direction of the laser emission propagation and the other being an output mirror located beyond the first mirror in the direction of the laser emission propagation; mounting units for mounting said mirrors so that they can rotate about two axes, one axis coinciding with the axis of the laser beam incident thereon and the other axis perpendicular to said one axis, the mirrors having means for rotation together in relation to the rotation axes of said input mirror, said mounting units also being mounted for variably adjusting the distance therebetween in order to change the distance between said mirrors along the axis of the laser beam reflected by the input mirror; an aiming grip mounted on said wavebeam guide for rotation about the axis of the laser beam reflected by said output mirror and for rotation together with said output mirror about the axis perpendicular to the axis of the laser beam incident on said output mirror; and a focusing lens mounted in said grip, said mirror mounting units securing said input and output mirrors at the ends of said wavebeam guide the axis of which coincides with the axis of the laser beam reflected by said input mirror, said wavebeam guide comprising a hollow telescopic shaft, and wherein the laser is located in an inclined position in relation to a vertical plane, means being associated with said hollow telescopic shaft of said wavebeam guide for movably and jointly securing the same as a movable cantilever to said mounting unit of said input mirror, said mounting unit of said input mirror including balancing means for balancing said telescopic shaft as a whole and said linearly movable portion thereof with said output mirror and said aiming grip.

* * * * *